(12) United States Patent
Harrah et al.

(10) Patent No.: US 10,441,785 B2
(45) Date of Patent: Oct. 15, 2019

(54) CONTROL OF BLADDER FUNCTION USING HIGH FREQUENCY PACING

(71) Applicant: Boston Scientific Scimed, Inc., Maple Grove, MN (US)

(72) Inventors: Timothy Harrah, Cambridge, MA (US); Ding He, Tyngsboro, MA (US); Sandra Nagale, Bolton, MA (US); Bryan Clark, Forest Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 15/228,580

(22) Filed: Aug. 4, 2016

(65) Prior Publication Data

US 2017/0036020 A1    Feb. 9, 2017

Related U.S. Application Data

(60) Provisional application No. 62/201,524, filed on Aug. 5, 2015.

(51) Int. Cl.
*A61N 1/36*    (2006.01)
*A61N 1/02*    (2006.01)
*A61N 1/05*    (2006.01)
*A61N 1/372*    (2006.01)

(52) U.S. Cl.
CPC ......... *A61N 1/36007* (2013.01); *A61N 1/025* (2013.01); *A61N 1/0514* (2013.01); *A61N 1/37217* (2013.01)

(58) Field of Classification Search
None
See application file for complete search history.

(56) References Cited

U.S. PATENT DOCUMENTS

| | | |
|---|---|---|
| 3,236,240 A | 2/1966 | Bradley |
| 8,295,933 B2 | 10/2012 | Gerber et al. |
| 2011/0190844 A1 | 8/2011 | Gerber |
| 2011/0301662 A1* | 12/2011 | Bar-Yoseph ......... A61N 1/0514 607/40 |
| 2013/0079840 A1 | 3/2013 | Su et al. |
| 2016/0278660 A1* | 9/2016 | Nagale .................. G06T 7/0012 |

FOREIGN PATENT DOCUMENTS

JP    2014521445 A    8/2014

OTHER PUBLICATIONS

Stewart WF et al., "Prevalence and burden of overactive bladder in the United States", World J Urol., (2003), vol. 20, 10 pages.
International Search Report and Written Opinion dated (Nov. 24, 2016), for PCT/US16/45557 (8 pages).

* cited by examiner

*Primary Examiner* — Kennedy Schaetzle (57) ABSTRACT

Systems and methods for the treatment of bladder conditions using direct electrical pacing are provided. The systems and methods generally apply high-frequency pacing stimuli directly to the bladder wall, from one or more of the inner and outer bladder surfaces.

17 Claims, 7 Drawing Sheets

CONTROL OF BLADDER FUNCTION USING HIGH FREQUENCY PACING

CROSS-REFERENCE TO RELATED APPLICATIONS

This application claims priority to U.S. Provisional Application Ser. No. 62/201,524, filed on Aug. 5, 2015, the entire disclosure of which is herein incorporated by reference.

FIELD OF THE INVENTION

This application relates to the field of medical devices and medical procedures. More particularly, the application is related to devices and methods for noninvasive electrophysiological treatment, for example of urological conditions.

BACKGROUND

The urinary bladder is a hollow, elastic organ that collects urine produced by the kidneys prior to urination (also referred to as "voiding" or "micturition"). The wall of the bladder generally includes an inner mucosal layer, a submucosal layer, and a muscular layer comprising, from inside-out, inner longitudinal, circular and outer longitudinal sublayers. Over the muscular layer are one or more connective tissue layers referred to as the serosa and adventitia. Between the bladder and the urethra is at least one bladder sphincter (the external bladder sphincter) that regulates the flow of urine from the bladder into the urethra during urination.

Contraction and relaxation of the bladder sphincter(s), and contraction of the bladder wall (also referred to as the "detrusor muscle") are controlled by both somatic and autonomic nervous systems and, on the autonomic side, by both the sympathetic and parasympathetic nervous systems. Sensory information from stretch receptors within the muscular layer of the bladder is conveyed by sensory afferents extending from the bladder to the pons, while efferent connections extend from the pons to the bladder by way of the pelvic nerve (parasympathetic) and/or the hypogastric nerve (sympathetic). Somatic control over voiding is mediated by the pudendal nerve, which innervates the external bladder sphincter and controls voluntary sphincter contraction and relaxation.

While normal bladder activity is easy to take for granted, it is an essential part of human physiology. Normal adults generally urinate around 6 or 7 times a day, typically during waking hours, though the frequency and timing of voiding can vary significantly between individuals. Overactive bladder ("OAB") is a condition in which normal voiding rhythm is disrupted, which is characterized by four symptoms: first, increased urgency to urinate, defined formally as a sudden, compelling desire to urinate that is difficult to deter; second, abnormal urinary frequency, defined as urination more than eight times per day; third, interruption of normal sleep by the urge to void, referred to as "nocturia;" and fourth, "urge incontinence" or involuntary voiding of the bladder during periods of urinary urgency. In the United States, OAB affects an estimated 16% of adults, and about 6% of adults suffer from OAB characterized by urge incontinence. (See Stewart W F, et al. Prevalence and burden of overactive bladder in the United States. *World J Urol*. May 20, 2003; (6):327-36.)

OAB has a variety of potential causes which are generally classified as myogenic (arising in the smooth muscle of the bladder), neuropathic (arising from the nervous system), mixed, or idiopathic (lacking a clear etiology). Notwithstanding these categorizations, electrical changes including increased spontaneous contractility and greater electrical coupling between myocytes are observed in detrusor muscle samples taken from patients with both neuropathic and non-neuropathic OAB.

Current treatments for OAB include behavioral therapy to include control over urgency and/or to improve bladder capacity; pharmacotherapy with anticholinergic drugs (e.g. darifenacin, fesoterdione, oxybutynin, etc.) or neurotoxins (e.g. onabotulinumtoxin-A); and electrical neuromodulation of the sacral nerve (for instance, using the InterStim® neuromodulator device (Medtronic, Inc. Minneapolis, Minn.)). While these interventions may be effective to treat OAB in some patients, current pharmacotherapies require repeated administration, while both pharmacological and neuromodulation approaches offer systemic, rather than targeted, intervention, and are accompanied by an increased risk of side effects.

SUMMARY OF THE INVENTION

The present invention, in its various aspects, provides targeted interventions for treating OAB that utilize high-frequency pacing to drive bladder function directly. In contrast to the systemic interventions currently used to treat OAB, the aspects of the present invention are minimally invasive and offer a reduced risk of side effects.

In one aspect, the present invention relates to a system for treating a patient that includes at least one electrode assembly comprising a retentive element for fixedly positioning the electrode assembly adjacent to, on or within the wall of the bladder and a controller in communication with the electrode and programmed to deliver, through an electrode within the at least one electrode assembly, electrical stimulation at a frequency of 300 Hz or greater. In some cases, the at least one electrode assembly is also able to record (i.e. to receive or detect, optionally amplify, filter or otherwise process, and/or transmit) an electrical signal in the bladder. In some cases, the retentive element is selected from: clip, a pin, a suture, a staple, a tissue adhesive, a patch, a button, an expandable wrap, a spiral or helical body at least partially insertable into the bladder wall, a hooked body at least partially insertable into the bladder wall, a plurality of magnetic elements disposed on opposite sides of the bladder wall or and a suction element. Alternatively or additionally, the one or more electrodes assemblies may be configured to adhere to the serosal surface of the bladder, and/or the electrode may have a penetrating element for delivering current into the wall of the bladder. The controller, meanwhile, optionally includes a wireless antenna and at least one of a high-frequency pulse generator and/or a pacing programmer; the inclusion of such features along with the ability to receive wireless instructions are useful in embodiments where the controller is implanted in the patient or carried by the patient. The electrode assembly or assemblies may also include a pressure sensor that communicates with the controller. In addition, or alternatively, the electrode assembly may also include an accelerometer to detect when the patient is moving (e.g., exercising, running etc.). In some cases, the system includes a plurality of electrode assemblies, each including at least one electrode. In these embodiments, the electrodes may be activated separately, and/or the controller may be configured to receive a recorded electrical signal from a first electrode and to deliver stimulation via a second electrode. Alternatively or additionally, the controller may deliver either high-frequency (300 Hz or greater) or low frequency (10 Hz or less, but greater than zero Hz)

stimulation in response to an input, or may deliver stimulus at one or more specific times based on a user-recorded information. The controller optionally or additional receives input wirelessly. Systems according to this aspect of the invention are suitable for, among other things, the treatment of overactive bladder.

In another aspect, the present invention relates to a method of treating a patient that includes activating an electrode contacting a wall of the bladder of the patient, thereby inhibiting spontaneous electrical activity within the bladder. The electrode may contact the inner and/or outer (external) bladder surfaces, and may be activated in response to an electrical signal in the bladder, which signal is optionally detected by the electrode. In some cases, the electrode is positioned near the bladder trigone or the bladder neck, or a nerve ending.

In yet another aspect, the present invention relates to a method of reducing a symptom of overactive bladder in a patient in need thereof, which method includes activating at least one electrode contacting a wall of a patient's bladder, providing high frequency (>300 Hz) pacing stimulation thereto. The at least one electrode may be activated in response to an input selected from: a user input, a spontaneous electrical activity measured by the at least one electrode, a pressure within the bladder above a predetermined threshold, and an instruction generated by a pre-programmed stimulation algorithm. Alternatively or additionally, the at least one electrode may contact one or more of the bladder neck and bladder trigone. In some cases, multiple electrodes may be used in the system, which electrodes may contact the bladder wall, and may optionally be activated independently of one another (e.g. through the use of a multi-channel controller). In some cases, the electrode or electrodes may provide high frequency stimulation with low amplitude; low frequency stimulation with high amplitude; or high frequency stimulation with high amplitude.

DRAWINGS

Aspects of the invention are described below with reference to the following drawings in which like numerals reference like elements, and wherein.

Unless otherwise provided in the following specification, the drawings are not necessarily to scale, with emphasis being placed on illustration of the principles of the invention.

DETAILED DESCRIPTION OF THE PREFERRED EMBODIMENTS

Figure 1A:
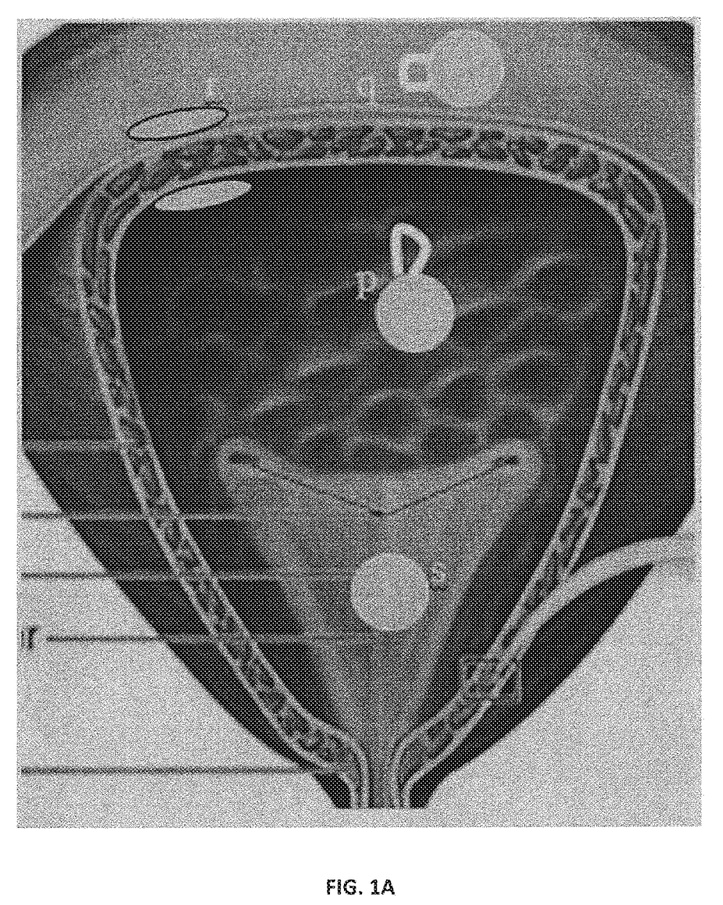
FIG. 1A is a schematic depiction of the urinary bladder in cross section, illustrating placement of pacing electrodes according to various embodiments of the present invention.

Systems and methods of the present invention are distinguished from currently-used neuromodulation systems by, among other things, the application of stimulus directly to the bladder, rather than to upstream efferents such as the sacral nerve, which may innervate sites other than the bladder. The direct delivery of current is achieved in various embodiments of the present invention by placement of electrodes on various bladder surfaces and in various bladder regions. FIG. 1A illustrates several exemplary electrode approaches and placements. It will be understood that, some embodiments of the present invention may involve the placement of a single electrode assembly at one of the sites illustrated, while other embodiments will involve the placement of multiple electrode assemblies at two or more of the sites illustrated. In some cases, as illustrated by reference character p, an electrode is placed on the mucosal surface of the bladder; alternatively or additionally, as shown by reference character q, an electrode is placed on the serosal surface of the bladder, and/or an electrode assembly comprising two elements is placed on either side of the bladder wall (reference character r). The electrode assembly may contact the surface of the bladder wall, or may include a penetrating element that extends into the bladder wall, such that the electrode, when deployed within the assembly, is adjacent to nerve endings within the muscular layer of the bladder wall; in some cases, the electrode assembly is sized so as to be fully implantable within the bladder wall, and may comprise, for instance, a microchip or a nanochip that is injectable into the bladder wall. And, in some cases, an electrode is positioned on or near one or more of the pudendal nerve and the external bladder sphincter.

In preferred embodiments, at least one electrode assembly is positioned in an anatomical region of the bladder characterized by a relatively high density of innervation. For example, reference character s depicts an electrode assembly deployed on the bladder trigone or bladder neck, which areas are characterized by relatively dense innervation. The electrode assemble may include, by way of non-limiting example, a band which provides 360° coverage of the trigone region on the serosal surface. In some cases, the site or sites at which the electrode assembly or assemblies are placed is determined by electrical and/or visual bladder mapping. Alternatively or additionally, a plurality of electrode assemblies is arrayed about at least a portion of the bladder wall, whereupon the electrodes can be driven and/or recorded from, individually or in multiples, to identify one or more sites where spontaneous electrical activity is increased (or decreased) relative to other regions of the bladder. Once these sites are identified, individual electrodes or groups of electrodes can be selected to provide optimal stimulation thereto.

Electrodes utilized in the various embodiments can be unipolar or bipolar, the latter being preferred where the electrodes assemblies include microstimulators. In some instances, an array of electrodes, in which each electrode or electrode assembly includes a microstimulator, is positioned within the bladder and a single element (e.g. a central element) is used as the cathode while one or more other elements in the array are used as one or more anodes. In preferred embodiments, the electrode(s) can be used for both stimulation and recording. In one group of embodiments, the electrode(s) record spontaneous bladder activity and, when a specific waveform or level of activity is detected, one or more electrodes switch to deliver stimulation. In another group of embodiments, stimulation is delivered in response to a sensed pressure (e.g. a pressure above a pre-set threshold, In another, related group of embodiments, the electrode(s) are activated by a user, particularly a patient or a health-care provider, to provide stimulation. In these cases, control of the electrodes, the pulse generator and the stimulation programmer may be mediated by customized hardware and/or software, or by an application running on a general purpose computer. Specifically, in some embodiments, stimulation can be triggered by a phone app. Additionally, the system 100 can be used in some cases to deliver low-frequency stimulation to assist in voiding: for instance, a user (such as a patient with difficulty in voiding fully) may trigger low-frequency stimulation in order to stimulate bladder contractions that aid in voiding. Alternatively, the system may deliver high frequency stimulation to reduce activity when exercising etc.

Where multiple electrodes or assemblies are used, they are preferably (though not necessarily) capable of being driven independently (for instance, by means of a multi-channel controller), so that one or more electrodes can be used for stimulation while, simultaneously, one or more electrodes are used for recording.

The electrode assemblies are preferably secured in place on the bladder wall to prevent migration or release, and may be secured using a clip, a pin, a suture, a staple, a tissue adhesive, a spiral or helical element similar to those used in cardiac pacing leads, a talon- or fishhook element as used in leadless pacemaker devices, a suction element, quills, and/or any other suitable securement means. The securement means is preferably robust enough to hold the electrode in place and resist displacement due to bladder contraction and/or fluid flows. In some cases, as illustrated by reference character r in FIG. 1, the electrode assembly sandwiches the bladder wall, and includes at least one structure for retaining the electrode, e.g. a magnetic plate, or a magnetic bead or beads which are injected into the bladder wall, or an element that is insertable into the bladder wall and that resists retraction, such as an element that is expanded once deployed.

Figure 1B:
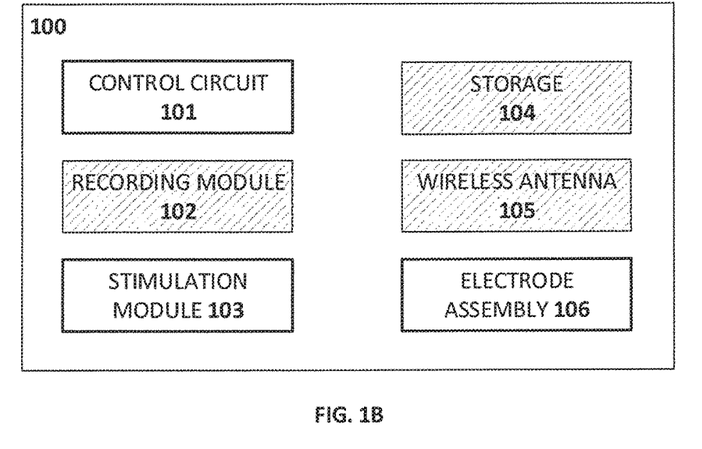
FIG. 1B is a schematic depiction of a pacing system according to certain embodiments of the present invention.

Turning now to FIG. 1B, an exemplary pacing system 100 includes, for example, a control mechanism such as a control circuit 101, a mechanism for delivering stimulation (stimulation module 103) and an electrode assembly 106 that includes at least one electrode and one or more of a microstimulator and/or a retention element. The system can also include one or more of a recording module 102 to facilitate electrical recording using the electrode assembly 106, storage means 104, and/or a wireless antenna 105 for receiving input, such as programming or triggering by a user. Communication between the system 100 and a user or another device can alternatively be mediated by a wired connection (not shown), or by optical or auditory means (not shown), among other possibilities. In certain embodiments, at least a portion of the system is portable and can be worn or carried by a patient. For example, system components may be carried by a belt, pack, or may be implanted within a body cavity of the patient. In some cases, the electrode(s) are physically separated from other components of the system, and are electrically coupled by means of one or more wires, or by means of a wireless antenna.

Figure 1C:
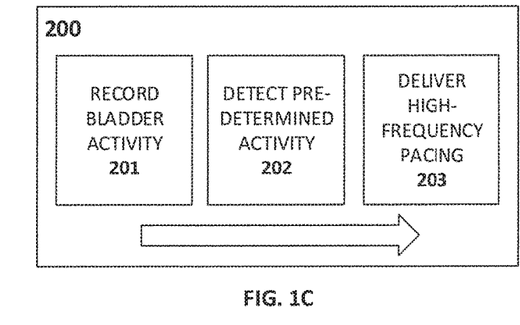
FIG. 1C and FIG. 1D depict pacing processes according to certain embodiments of the present invention.
Figure 1D:
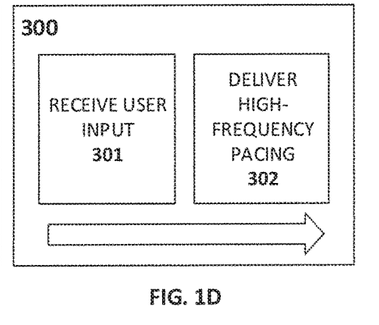

In use, the system 100 delivers intermittent high-frequency (e.g. 300 Hz and above) pacing to the bladder wall to reduce or eliminate aberrant electrical activity that contributes to OAB. Pacing stimuli are delivered over a period of seconds to minutes, and can be triggered by a user, in response to a feeling of urgency (e.g., as illustrated by the scheme 300 in FIG. 1D whereby received user input 301 is used to deliver high frequency pacing 302), or by a microcontroller (which may be part of control circuit 101 or, alternatively, may communicate with system 100 by means of the wireless antenna 105) in response to a recorded electrical activity (e.g., as shown in the scheme 200 of FIG. 1C, whereby recorded bladder activity 201 is analyzed and, in the event that a given predetermined activity is detected 202, high frequency pacing is delivered 203), or other triggering event. Pacing stimuli can also be delivered in some cases based on user recorded information such as an electronic patient voiding diary or a sensor that logs voiding events (e.g. pad wetness sensor, GPS sensor indicating visit to bathroom, posture sensor). In one example, the system 100 registers voiding events throughout a period of time and an algorithm 'learns' the patient's voiding pattern and triggers stimulus (and adjusts frequency and electrode location, if there are multiple electrodes) in time to prevent further undesired voiding events. The system 100 is preferably durable enough to provide periodic stimulation to the bladder over months or years, and to simplify periodic maintenance tasks such as replacement of batteries or consumable parts. Charging of the system 100 may also be done periodically by a user, without the need to remove the system or change any batteries. For instance, in some embodiments, an induction charging antenna system is used to provide wireless charging of the system. In some cases, a component of the antenna system such as a charging mat is configured to be disposed within an article of clothing (e.g. a shirt or jacket) or an article of bedding (e.g. a sheet or blanket) used by the patient, thus permitting charging of the system during daily activities or during sleep. Such an arrangement may offer a significant advantage over other prospective OAB treatments by reducing the risk of a loss of system power, and thus of system efficacy, at a time when the patient experiences the symptoms of OAB such as urgency, urge incontinence, or nocturia.

The principles of the present disclosure and its various embodiments are further illustrated in the following non-limiting examples:

Example 1: Establishing a Canine Model of Bladder Function

The inventors utilized a canine bladder model to (i) measure and record biological signals in healthy bladder tissue and to correlate active signal sites with the electrode locations within the bladder and (ii) measure local electrical activity in multiple foci in the bladder wall of a healthy canine with both normal saline instillation and subsequent instillation of capsaicin irritant to acutely mimic overactive bladder. Two female mongrel canines were used for the study. A 128-channel electrophysiology Lab System Pro recording system (Boston Scientific, Marlboro, Mass.) and a MicroPace EP stimulator (Sydney, Australia) were used to record the electrical signals and perform the electrical stimulation in the bladder. The EP recording system was set to measure and record both conventional and the reverse electrode polarity in all bipolar settings. A Grass electrical stimulator was also used for the high frequency stimulation at 300 Hz.

Recordings of bladder activity were made using a 75-mm 64 electrode array Constellation catheter (Boston Scientific, Marlboro, Mass.) that was used for the intra-bladder recording. The inventors also tested a 10-elecrode Dynamic Deca catheter and a 14-electrode Orbiter PV catheter.

In each animal, the bladder was filled with physiological saline at room temperature. Electrophysiology catheters were placed at the different bladder volumes e.g. 50, 100, 150, 200 and 300 ml respectively the inventors attempted throughout to maintain optimal electrode-tissue contact during the measurements. Fluoroscopic images were obtained and stored that correlate the catheter placement at the relevant anatomic positions for the post procedure analysis. Intra-bladder and rectal pressure were also measured and recorded.

Example 2: Baseline Measurements of Bladder Activity

Figure 2A:
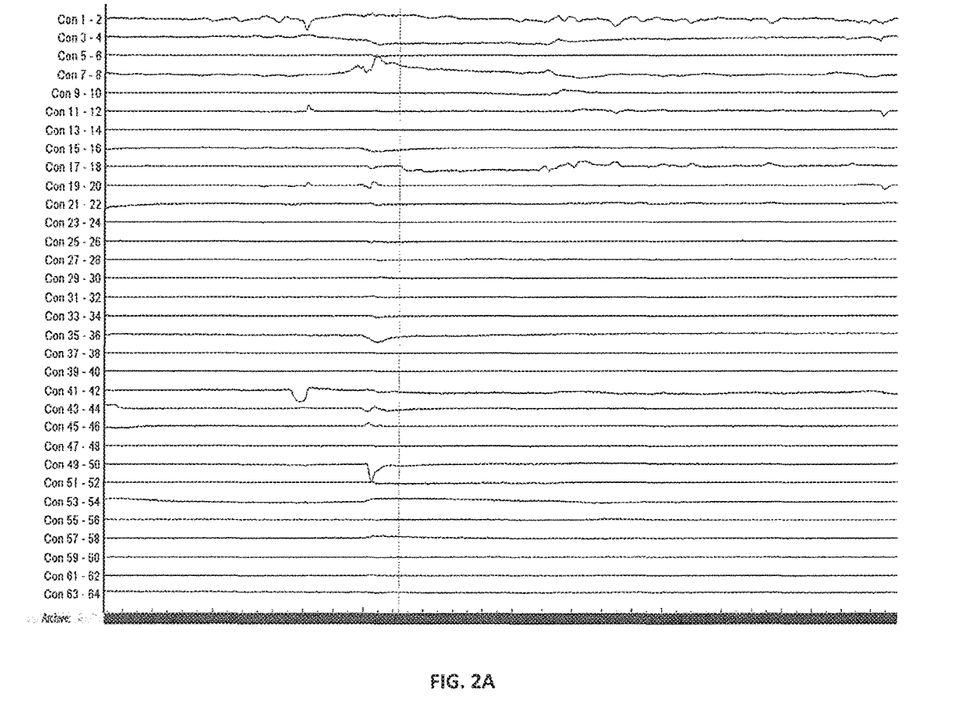
FIGS. 2A and 2B show a series of electrical recordings made in canine bladder prior to pacing according to certain embodiments of the present invention.
Figure 2B:
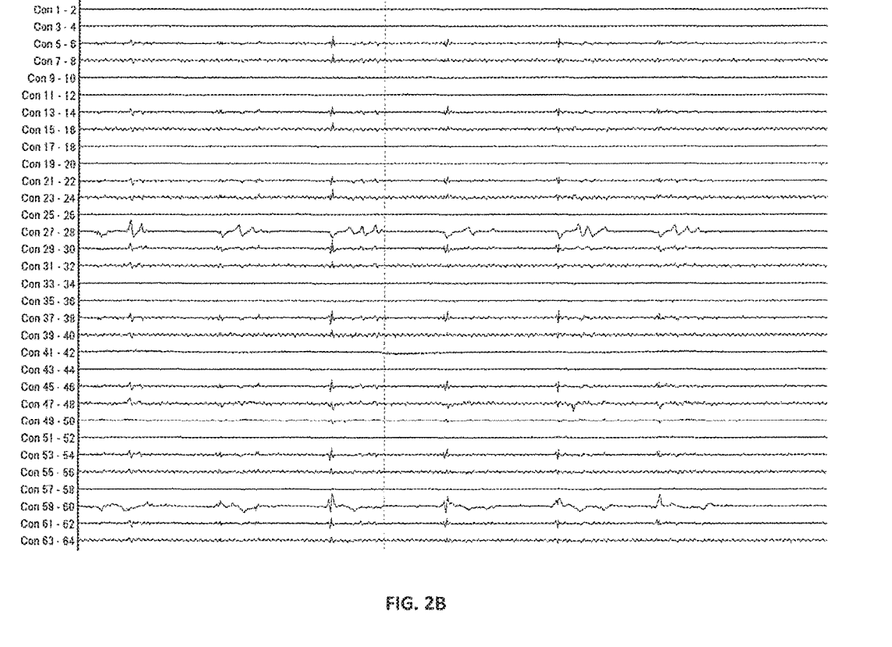

Spontaneous electrical signals, as shown in FIG. 2A (100 mL bladder volume) and FIG. 2B, at were observed in both experimental animals, and appeared substantially random, as described previously by others. However, spontaneous electrical activity appeared to be greater during the early phase of the experiment, and were noticeably reduced during the late phase of the experiment. While the traces in FIG. 2A also show motion artefacts, the inventors note that these are readily distinguishable from spontaneous electrical activity on the basis of timescale and/or amplitude.

Recordings were made at various bladder volumes from 50 mL to 300 mL, and the inventors observed that spontaneous electrical activity was increased during periods when bladder volume was varied (i.e. increased) relative to periods when the bladder volume was held substantially constant. Without wishing to be bound by any theory, these results suggest that local distortions of the bladder wall that accompany changes in volume may stimulate bladder afferent activity.

Example 3: Low- And High-Frequency Pacing of Canine Bladder

Figure 3A:
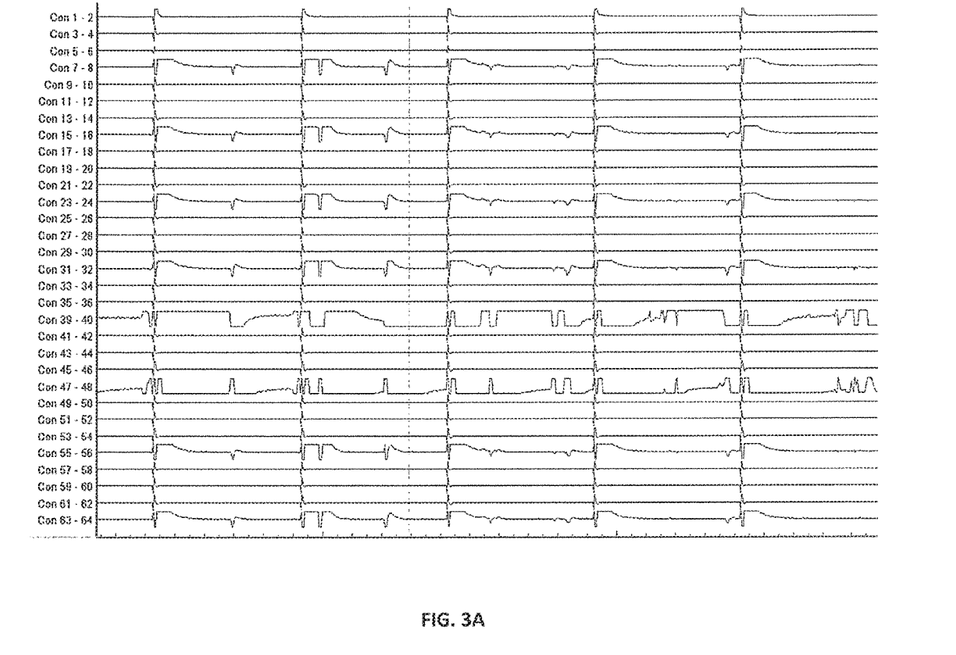
FIGS. 3A, 3B and 3C show electrical recordings made in canine bladder following application of a (A) low-frequency and (B-C) high-frequency pacing stimulus according to certain embodiments of the present invention.
Figure 3B:
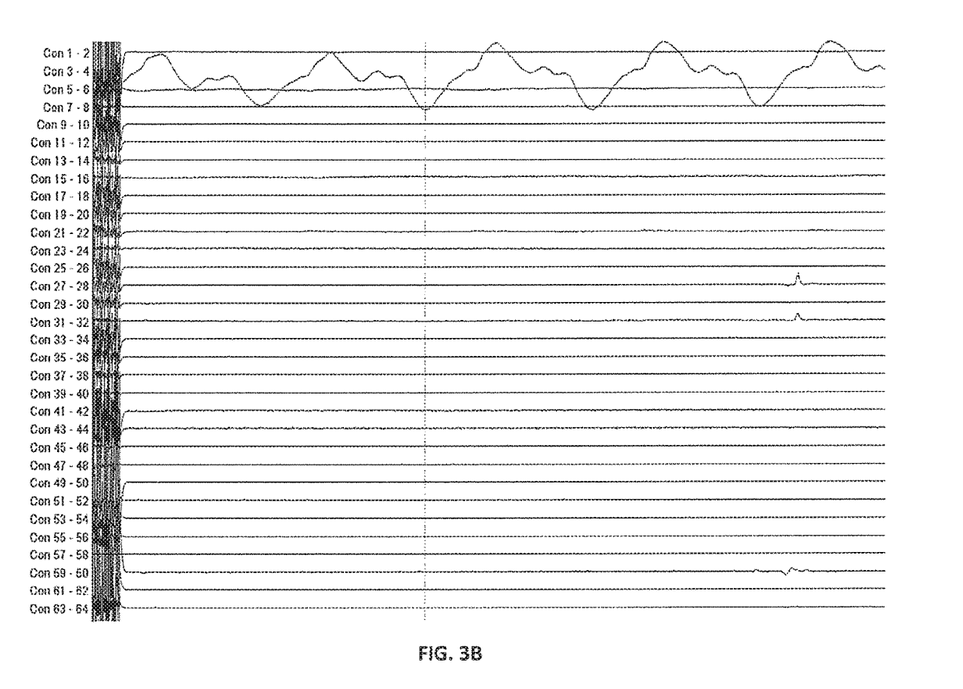
Figure 3C:
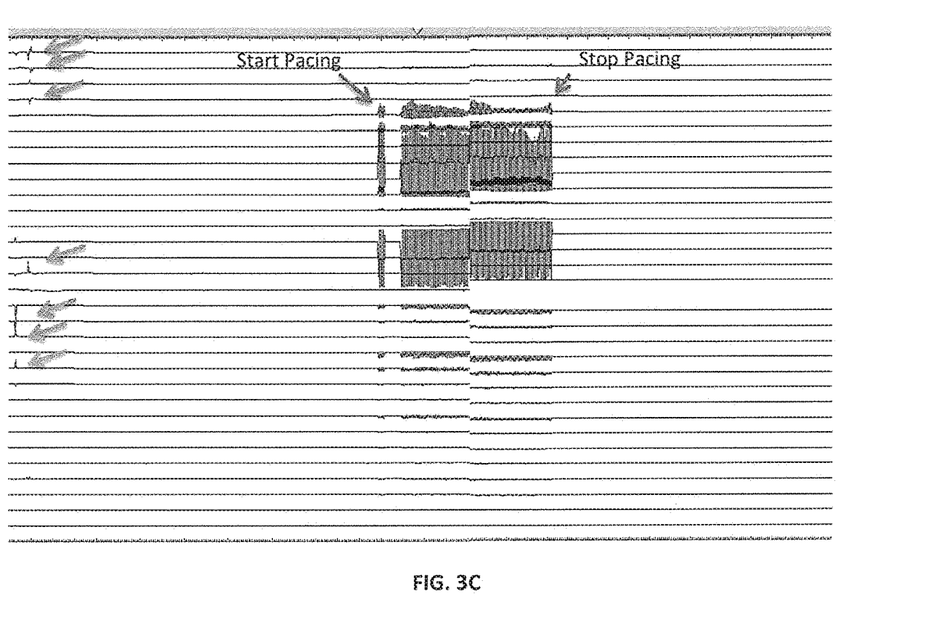

Low-frequency (2 Hz) pacing was applied to the bladder at 500 ms cycle length, as shown in FIG. 3A. Low frequency electrical stimulation (stimulus artefacts visible as periodic vertical deflections) activated local muscle contractions that, in some cases, underwent limited propagation. By contrast, FIG. 3B shows that the application of high frequency pacing (300 Hz) (stimulus artefacts visible on left), relatively fewer local electrical signals were observed, suggesting that high-frequency pacing, but not low frequency pacing, is sufficient in some cases to reduce spontaneous electrical activity in the bladder. This suggestion was reinforced by additional electrical recordings at high frequency pacing such as those shown in FIG. 3C. Prior to the high frequency stimulation, there were spontaneous activities (indicated by arrows) observed from different recording electrodes which reflected the electrical activities at different regions of bladder (see the left side of the figure). However, following a train of burst high frequency stimulation, no active electrical signals were observed, underscoring the efficacy of high frequency stimulation in inhibiting nerve fibers innervating the bladder muscle wall.

CONCLUSION

The foregoing examples have focused on pacing of the bladder to limit spontaneous electrical activity and, thereby, to treat OAB. Those of skill in the art, however, will understand that the embodiments illustrated above are useful in the treatment of a variety of conditions related to aberrant spontaneous electrical activity in bodily organs or lumens. For instance, electrodes and systems similar to those described above may be useful in treating conditions of the digestive tract, including without limitation the stomach and/or the large and small intestines. The use of the electrodes, systems and methods described above to treat such conditions are within the scope of the present invention.

The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The term "consists essentially of means excluding other materials that contribute to function, unless otherwise defined herein. Nonetheless, such other materials may be present, collectively or individually, in trace amounts.

As used in this specification, the term "substantially" or "approximately" means plus or minus 10% (e.g., by weight or by volume), and in some embodiments, plus or minus 5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

Certain embodiments of the present invention have described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

The invention claimed is:

1. A method of treating a patient, comprising:
   implanting an electrode on or within a bladder wall of the patient;
   sensing, with the implanted electrode, an aberrant electrical activity; and
   activating the implanted electrode to deliver a pacing signal on or within the bladder wall of the patient to inhibit the aberrant electrical activity.

2. The method of claim 1, wherein the electrode is implanted on or within an interior surface of the bladder wall.

3. The method of claim 1, wherein the electrode is implanted on or within an external surface of the bladder wall.

4. The method of claim 1, wherein the electrode is disposed on or within the bladder trigone or bladder neck.

5. The method of claim 1, wherein the electrode is disposed near a nerve ending.

6. The method of claim 1, wherein activating the electrode delivers an intermittent high-frequency pacing signal to inhibit the aberrant electrical activity.

7. The method of claim 1, wherein the aberrant electrical activity results from a feeling of urgency by the patient.

8. The method of claim 1, wherein the electrode is activated by the patient.

9. The method of claim 1, wherein the electrode is activated wirelessly.

10. A method of reducing a symptom of overactive bladder in a patient, comprising:
   implanting at least one electrode on or within a bladder wall of the patient;
   sensing, with the at least one implanted electrode, an input; and
   activating the at least one implanted electrode to provide a high-frequency pacing stimulation on or within the bladder wall to inhibit the input.

11. The method of claim 10, wherein the input is selected from the group consisting of a spontaneous electrical activity measured by the at least one electrode and a pressure within the bladder above a predetermined threshold.

12. The method of claim 10, wherein the at least one electrode is positioned to deliver electrical stimulation to at least one of the bladder neck and the bladder trigone.

13. The method of claim 10, wherein the at least one electrode includes a plurality of electrodes activated independently of one another.

14. The method of claim 10, wherein activating the at least one electrode delivers an intermittent high-frequency pacing signal to inhibit the input.

15. The method of claim 10, wherein the input results from a feeling of urgency by the patient.

16. The method of claim 10, wherein the at least one electrode is activated by the patient.

17. The method of claim 10, wherein the at least one electrode is activated wirelessly.

* * * * *